(12) United States Patent
Xie

(10) Patent No.: US 11,534,342 B2
(45) Date of Patent: Dec. 27, 2022

(54) COMBINATION AIR FILTER AND GOGGLES

(71) Applicant: Qinbo Xie, Guangdong (CN)

(72) Inventor: Qinbo Xie, Guangdong (CN)

( * ) Notice: Subject to any disclaimer, the term of this patent is extended or adjusted under 35 U.S.C. 154(b) by 337 days.

(21) Appl. No.: 16/894,925

(22) Filed: Jun. 8, 2020

(65) Prior Publication Data
US 2020/0297538 A1    Sep. 24, 2020

(30) Foreign Application Priority Data

Mar. 19, 2020   (CN) ......................... 202020353281.X

(51) Int. Cl.
| | | |
|---|---|---|
| *B01D 46/00* | (2022.01) | |
| *B01D 46/42* | (2006.01) | |
| *A61F 9/02* | (2006.01) | |
| *A61L 9/20* | (2006.01) | |

(52) U.S. Cl.
CPC .............. *A61F 9/028* (2013.01); *A61F 9/025* (2013.01); *A61F 9/027* (2013.01); *A61F 9/029* (2013.01); *A61L 9/20* (2013.01); *B01D 46/0028* (2013.01); *B01D 46/0043* (2013.01); *B01D 46/4245* (2013.01); *A61L 2209/12* (2013.01); *A61L 2209/14* (2013.01)

(58) Field of Classification Search
CPC ............ B01D 46/4245; B01D 2209/11; B01D 2209/14; B01D 2273/30; A61F 9/027; A61F 9/028; A61F 9/029; A61F 9/20
USPC ........ 55/486, 495, 385.1, DIG. 34, DIG. 35; 96/4, 117.5, 416, 417, 418; 128/202.22, 128/206.21; 422/68.1, 82.05, 83, 87, 88, 422/200.24; 429/119
See application file for complete search history.

(56) References Cited

U.S. PATENT DOCUMENTS

| | | | | |
|---|---|---|---|---|
| 2,573,722 | A * | 11/1951 | Maurer ................... | A61F 9/028 55/495 |
| 4,280,491 | A * | 7/1981 | Berg ...................... | A42B 3/288 55/DIG. 35 |
| 4,382,440 | A * | 5/1983 | Kapp .................... | A62B 17/04 55/486 |
| 4,462,399 | A * | 7/1984 | Braun .................. | A62B 18/045 55/DIG. 35 |
| 4,807,614 | A * | 2/1989 | van der Smissen ... | A62B 17/04 55/DIG. 35 |
| 5,042,474 | A * | 8/1991 | Williamson ....... | A41D 13/1184 55/DIG. 35 |
| 5,165,395 | A * | 11/1992 | Ricci .................. | A41D 13/1146 55/DIG. 35 |
| 6,338,340 | B1 * | 1/2002 | Finch .................... | A62B 18/084 128/206.28 |
| 8,821,621 | B2 * | 9/2014 | Dwyer ................. | G01N 21/783 55/DIG. 35 |

* cited by examiner

*Primary Examiner* — Minh Chau T Pham
(74) *Attorney, Agent, or Firm* — Westbridge IP LLC

(57) ABSTRACT

A combination air filter and goggles includes a pair of goggles; an air filter; a tube having a first end attached to the goggles and a second end attached to the air filter; a first strap having two ends attached to the air filter; and a check valve disposed on the goggles. The air filter includes a centrifugal fan, a circuit board, a UV lamp, a filter element, a power supply, a housing, and a cover. Clean air produced by the air filter may flow to inside of the goggles.

6 Claims, 6 Drawing Sheets

COMBINATION AIR FILTER AND GOGGLES

BACKGROUND OF THE INVENTION

1. Field of the Invention

The invention relates to medical equipment and more particularly to a combination air filter and goggles having improved characteristics.

2. Description of Related Art

Goggles are forms of protective eyewear that usually enclose or protect the area surrounding the eye in order to prevent particulates, water or chemicals from striking the eyes. The goggles may be used to absorb light waves of specific wavelength and allow other waves to pass through. Lenses of the goggles are tinted for protecting the eyes. The lenses of most goggles are absorptive and others are reflective.

Moisture may be formed on the lenses of the goggles. There are goggles having anti-fog lenses. However, the anti-fog function of the goggles is poor in practice. Further, microorganisms may quickly grow inside the goggles and excessive heat may be accumulated therein. Thus, the wearer may feel a degree of discomfort. Furthermore, airborne diseases can be transmitted through vents of the goggles. This is especially undesirable to medical employees.

Thus, the need for improvement still exists.

SUMMARY OF THE INVENTION

The invention has been made in an effort to solve the problems of the conventional art including moisture forming, poor ventilation, and transmission of airborne diseases by providing a combination air filter and goggles having novel and nonobvious characteristics.

To achieve above and other objects of the invention, the invention provides a combination air filter and goggles comprising a pair of goggles; an air filter; a tube having a first end attached to the goggles and a second end attached to the air filter; a first strap having two ends attached to the air filter; and a check valve disposed on the goggles; wherein the air filter includes a centrifugal fan, a circuit board, a ultraviolet (UV) lamp, a filter element, a power supply, a housing for enclosing the centrifugal fan, the circuit board, the UV lamp, the filter element, and the power supply, and a cover threadedly secured to the housing; and wherein the centrifugal fan is threadedly secured to the housing, the circuit board is threadedly secured to the centrifugal fan and are electrically interconnected, the UV lamp is disposed at an outlet of the centrifugal fan and is electrically connected to the circuit board, the filter element is disposed at an inlet of the centrifugal fan, and the power supply is disposed adjacent to a first side of the housing and is configured to supply electricity to the centrifugal fan, the circuit board, and the UV lamp.

Preferably, further comprises a second strap having two ends attached to two sides of the goggles respectively, and the check valve is disposed at a first side of the goggles.

Preferably, further comprises a push-button and a power-on light both disposed on the housing, and both the push-button and the power-on light are electrically connect to the circuit board.

Preferably, further comprises a power socket disposed on the housing so that mains power is configured to supply to the power supply for charging by electrically connecting to the power socket.

Preferably, further comprises an opening disposed through the circuit board and aligned with the inlet of the centrifugal fan.

Preferably, further comprises a plurality of louvers disposed on the cover, and a battery cover disposed adjacent to the louvers and aligned with the power supply.

The invention has the following advantageous effects in comparison with the prior art: air cleaning, moisture and excessive heat removal, anti-fog, a degree of freshness and comfort on the eyes of a wearer, preventing foul air from entering the goggles through the check valve, easy wearing on the body part, and the UV light being capable of inactivating bacteria, viruses, and protozoa.

The above and other objects, features and advantages of the invention will become apparent from the following detailed description taken with the accompanying drawings.

DETAILED DESCRIPTION OF THE INVENTION

Figure 1:
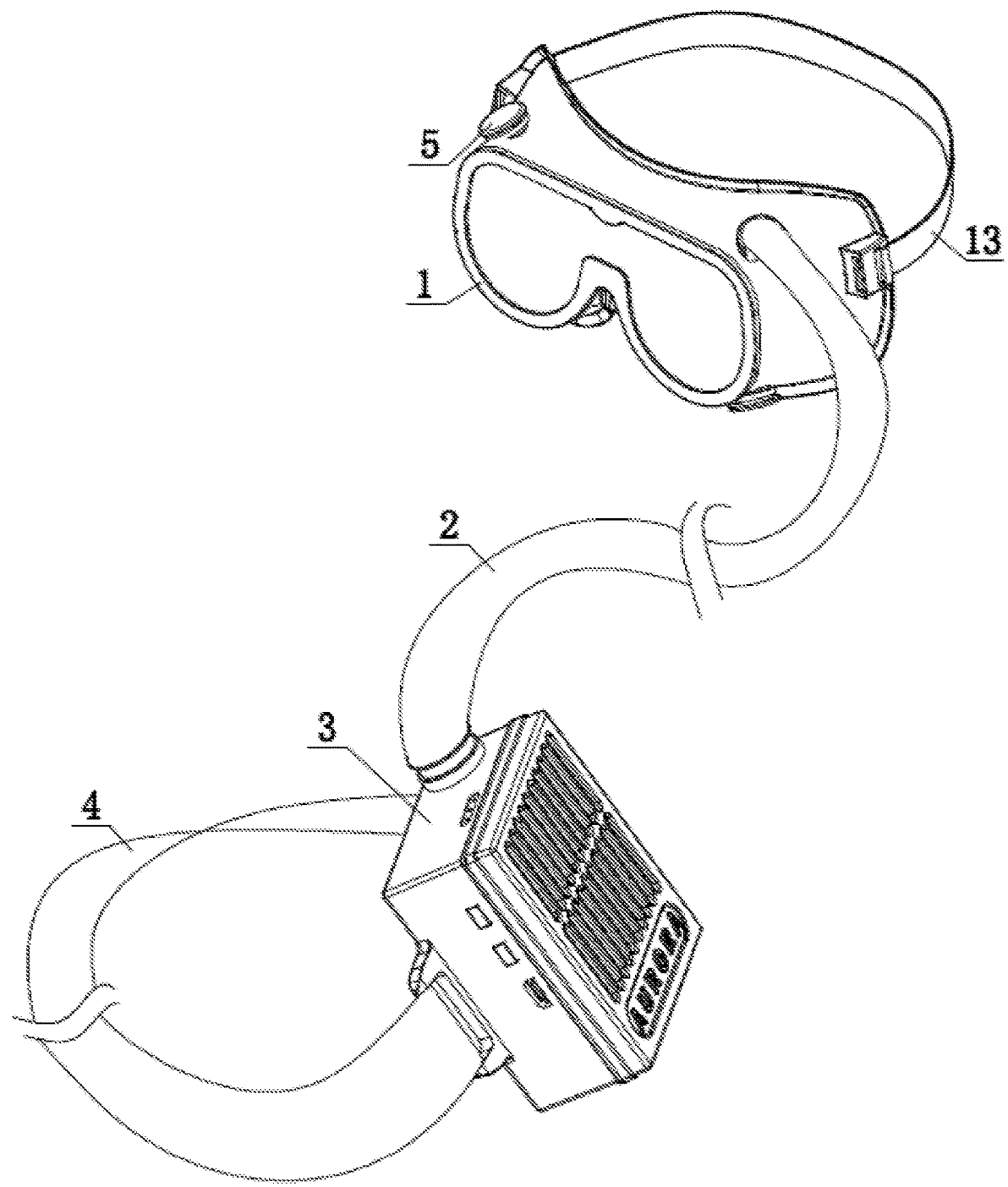
FIG. 1 is a perspective view of a combination air filter and goggles according to the invention.
Figure 2:
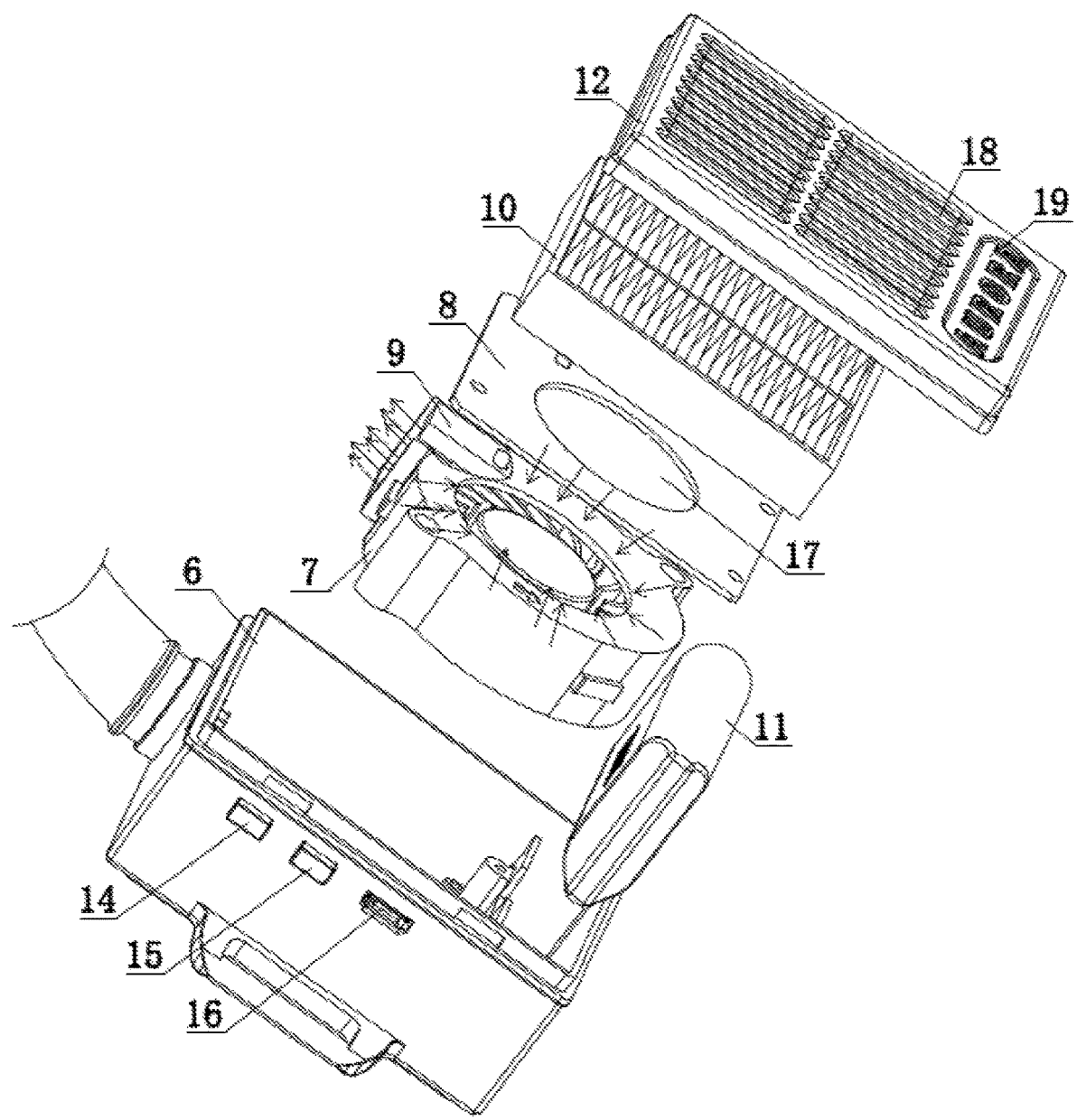
FIG. 2 is an exploded view of the air filter.
Figure 3:
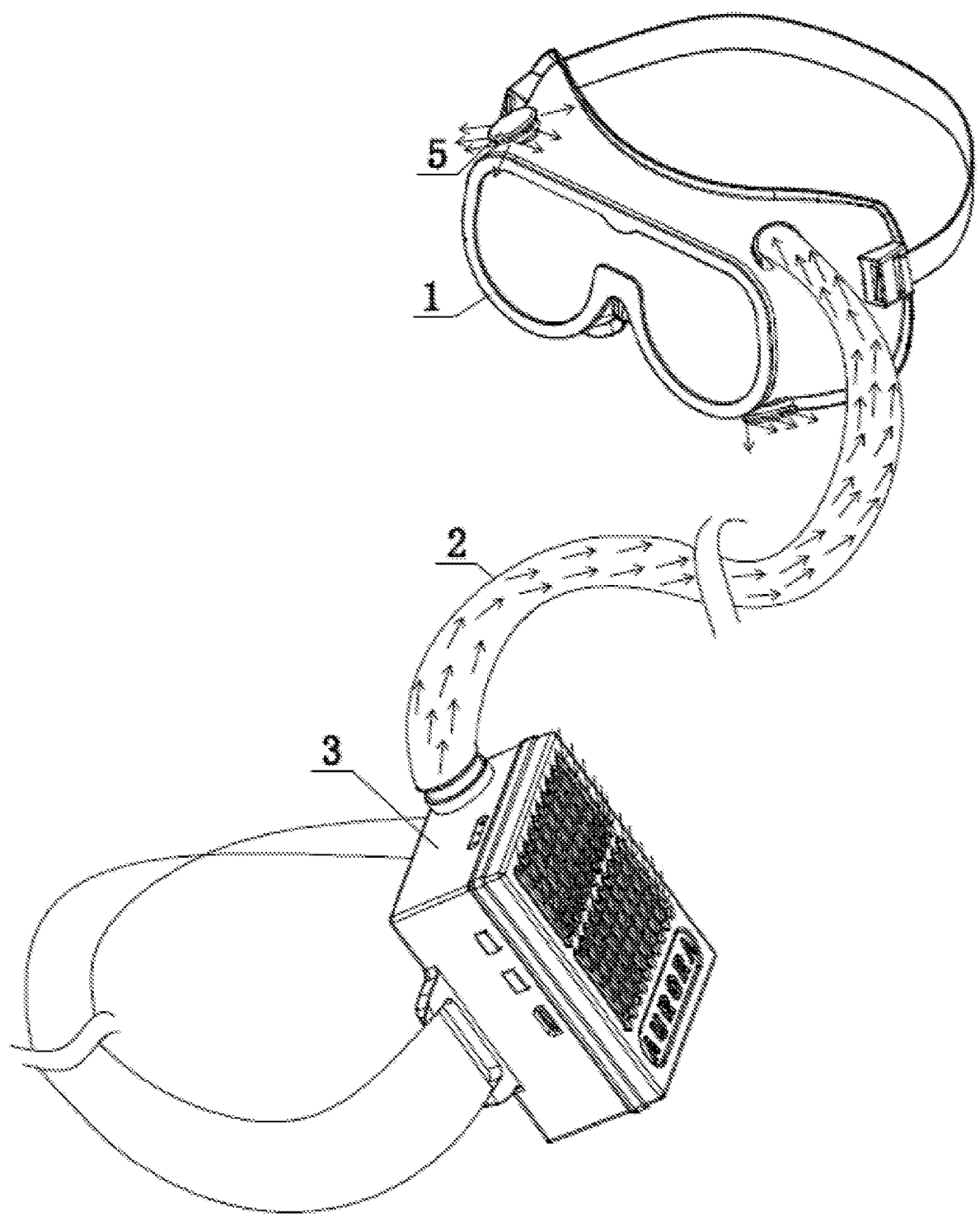
FIG. 3 is a view similar to FIG. 1 showing airflow through the tube.
Figure 4:
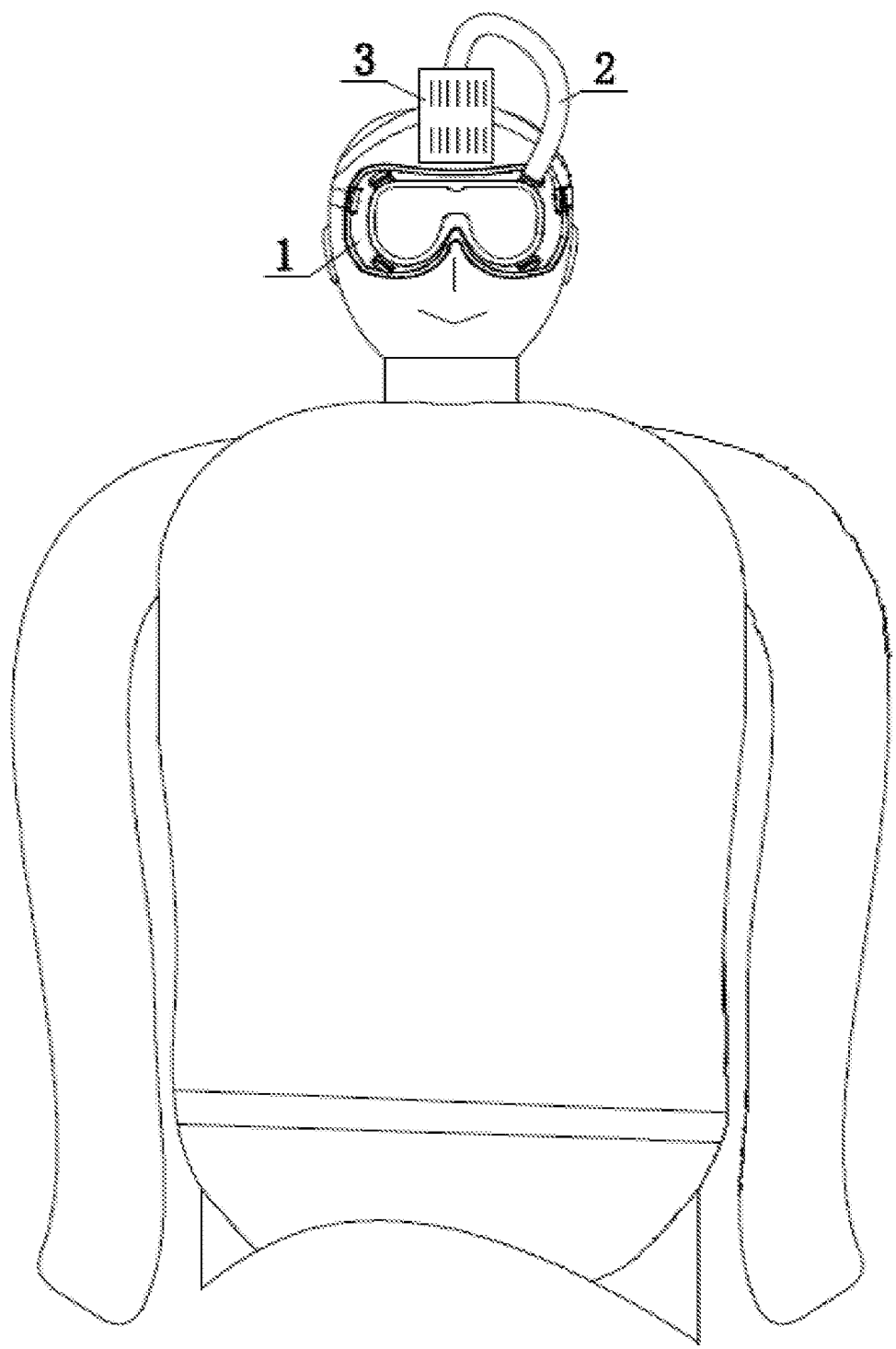
FIG. 4 is an environmental view showing a medical employee wearing the goggles and putting the air filter on the head.
Figure 4A:
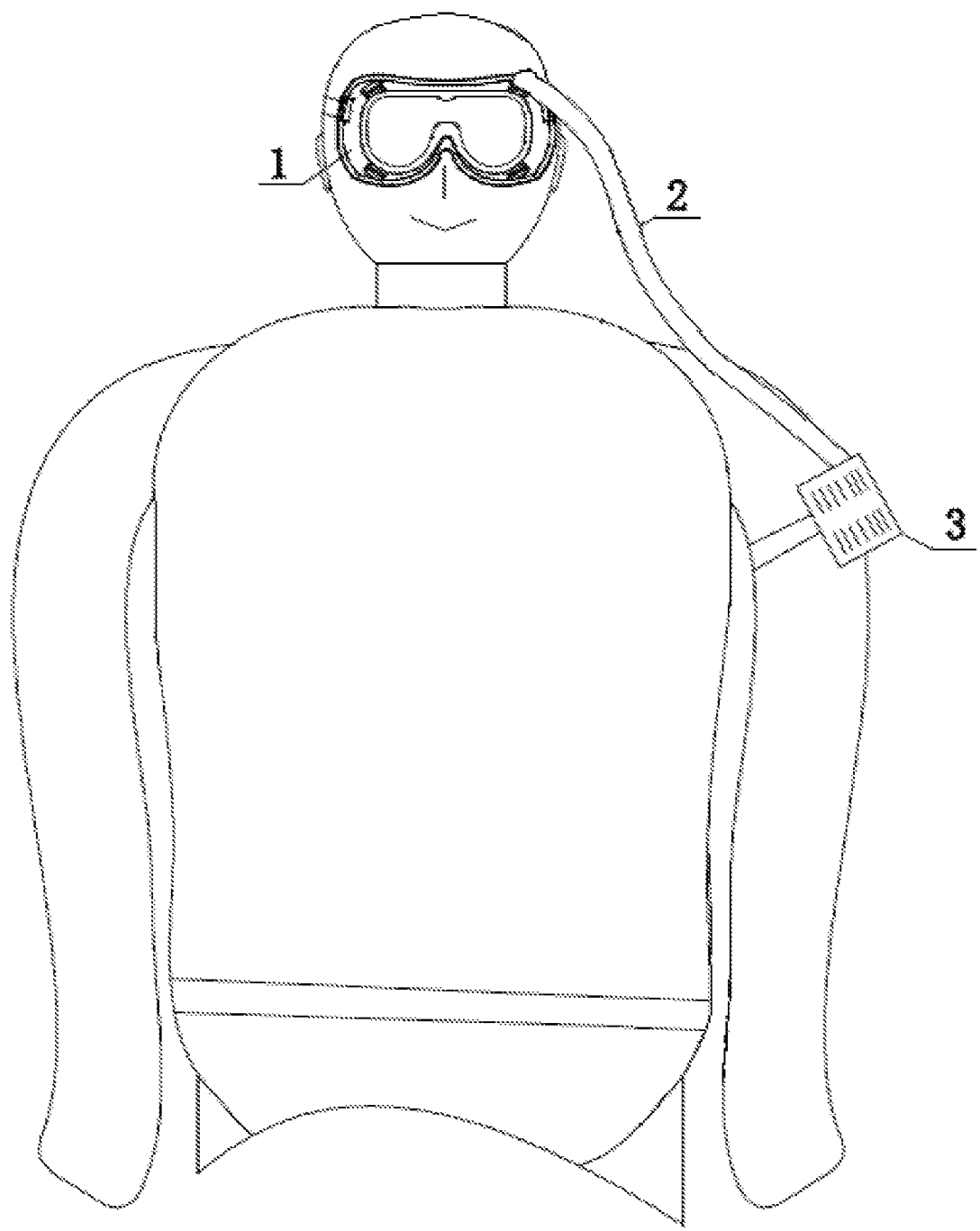
FIG. 4A is an environmental view showing a medical employee wearing the goggles and putting the air filter on the arm.
Figure 4B:
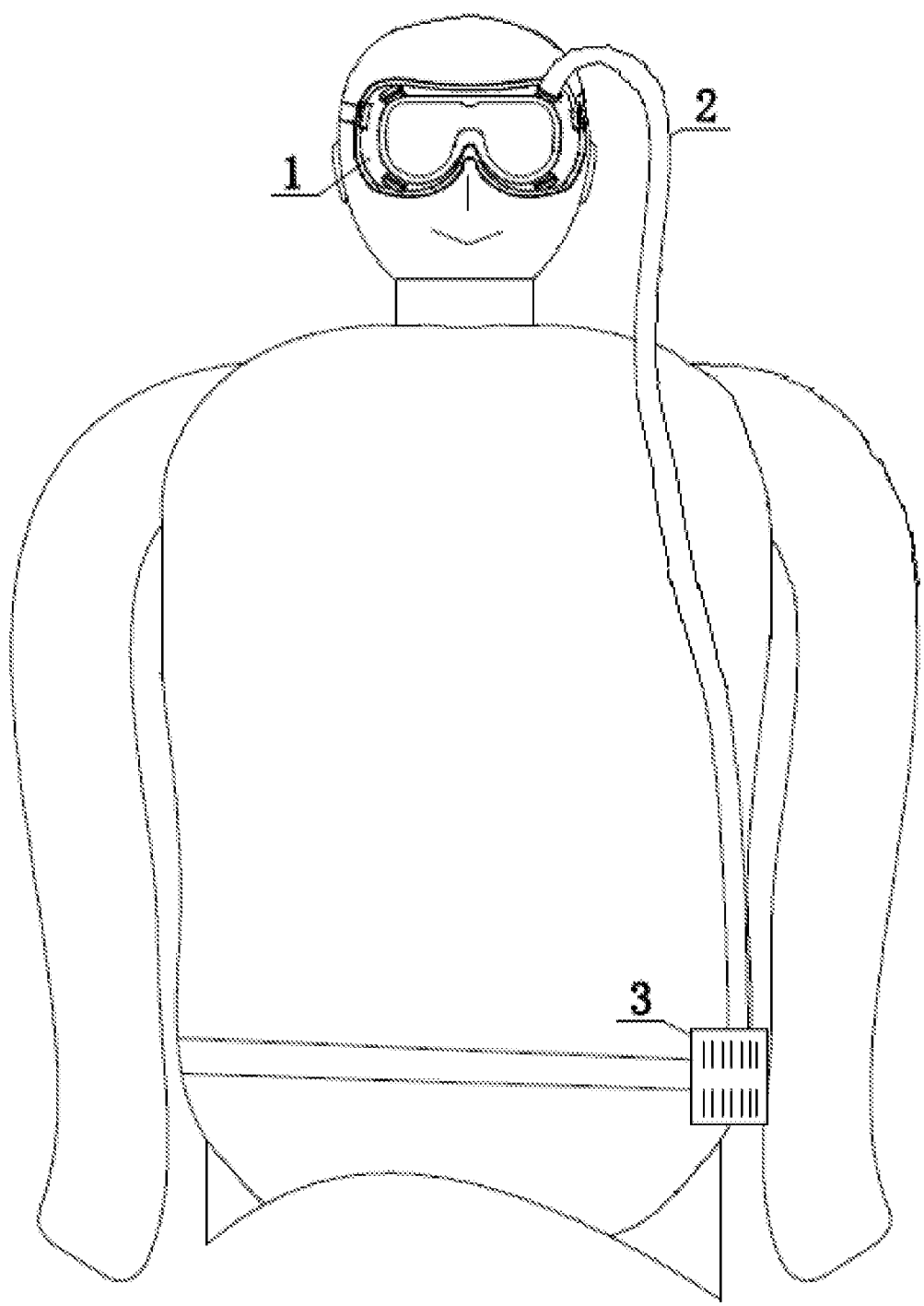
FIG. 4B is an environmental view showing a medical employee wearing the goggles and putting the air filter on the waist.

Referring to FIGS. 1 to 4B, a combination air filter and goggles in accordance with the invention comprises a pair of goggles 1, a tube 2, an air filter 3, a first strap 4 and a check valve 5 provided on the goggles 1 as discussed in detail below.

The first strap 4 has two ends attached to the air filter 3. A first end of the tube 2 is attached to the frame of the goggles 1 and a second end thereof is attached to the air filter 3. Clean air can flow from the air filter 3 to the goggles 1 through the tube 2. And in turn, the clean air expels moisture and excessive heat out of the goggles 1 through the check valve 5 while preventing foul air from entering the goggles 1 through the check valve 5. As a result, a wearer may feel a degree of freshness and comfort on his or her eyes.

The air filter 3 includes a centrifugal fan 7, a circuit board 8 for control purposes, a ultraviolet (UV) lamp 9, a filter element 10, a power supply (e.g., rechargeable battery) 11, a housing 6 for enclosing the above components, and a cover 12 threadedly secured to the housing 6. The centrifugal fan 7 is threadedly secured to the housing 6. The circuit board 8 is threadedly secured to the centrifugal fan 7 and they are electrically interconnected. The UV lamp 9 is disposed at an outlet of the centrifugal fan 7 and is electrically connected to the circuit board 8. The filter element 10 is disposed at the inlet of the centrifugal fan 7. The power supply 11 is disposed adjacent to one side of the housing 6 and is used to supply electricity to the centrifugal fan 7, the circuit board 8 and the UV lamp 9. The first strap 4 has two ends secured to the air filter 3 so that a medical employee may put the first strap 4 on his or her head, arm, or waist. The UV lamp 9 is used to produce UV light which can inactivate bacteria, viruses, and protozoa.

Further, a second strap 13 has two ends attached to two sides of the goggles 1 respectively. The check valve 5 is disposed at one side of the shield of the goggles 1. A wearer may put the second strap 13 on his or her head to wear the goggles 1.

Furthermore, a push-button 14 and a power-on light 15 are provided on the outer surface of the housing 6 and they are electrically connect to the circuit board 8. A pressing of the push-button 14 may activate the air filter 3. The power-on light 15 may light when the power supply 11 is activated.

In addition, a power socket 16 is provided on the outer surface of the housing 6 adjacent to the power-on light 16. Mains power may be supplied to the power supply 11 for charging by inserting an end of a power cord into the power socket 16. The power supply 11 is used to supply electricity to all components of the air filter 3. A circular opening 17 is provided through the circuit board 8 and aligned with the inlet of the centrifugal fan 7 so that fresh air produced by the centrifugal fan 7 may pass through the opening 17. A pressing of the push-button 14 may cause the circuit board 8 to activate the centrifugal fan 7. Louvers 18 are provided on the cover 12 for bringing fresh air to the inlet of the centrifugal fan 7, and a battery cover 19 is provided adjacent to the louvers 19 and aligned with the power supply 11. The battery cover 19 can be opened prior to removing the power supply 11 from the air filter 3.

An operation of the invention is discussed in detail below. A medical employee may put the second strap 13 on his or her head to wear the goggles 1 and put the first strap 4 on his or her head (see FIG. 4). The employee may press the push-button 14 to activate the circuit board 8 which in turn activates the centrifugal fan 7 to draw air through the filter element 10 which removes solid particulates such as dust, pollen, mold, and bacteria from the air. The activated UV lamp 9 near the outlet of the centrifugal fan 7 produces UV light which can inactivate bacteria, viruses, and protozoa. The clean air flows to the goggles 1 through the tube 2. And in turn, the clean air expels moisture and excessive heat out of the goggles 1 through the check valve 5 while preventing foul air from entering the goggles 1 through the check valve 5. A. As a result, the employee may feel a degree of freshness and comfort on his or her eyes.

While the invention has been described in terms of preferred embodiments, those skilled in the art will recognize that the invention can be practiced with modifications within the spirit and scope of the appended claims.

What is claimed is:

1. A combination air filter and goggles, comprising:
    a pair of goggles;
    an air filter;
    a tube having a first end attached to the goggles and a second end attached to the air filter;
    a first strap having two ends attached to the air filter; and
    a check valve disposed on the goggles;
    wherein the air filter includes a centrifugal fan, a circuit board, a ultraviolet (UV) lamp, a filter element, a power supply, a housing for enclosing the centrifugal fan, the circuit board, the UV lamp, the filter element, and the power supply, and a cover threadedly secured to the housing; and
    wherein the centrifugal fan is threadedly secured to the housing, the circuit board is threadedly secured to the centrifugal fan and are electrically interconnected, the UV lamp is disposed at an outlet of the centrifugal fan and is electrically connected to the circuit board, the filter element is disposed at an inlet of the centrifugal fan, and the power supply is disposed adjacent to a first side of the housing and is configured to supply electricity to the centrifugal fan, the circuit board, and the UV lamp.

2. The combination air filter and goggles of claim 1, further comprising a second strap having two ends attached to two sides of the goggles respectively, and wherein the check valve is disposed at a first side of the goggles.

3. The combination air filter and goggles of claim 1, further comprising a push-button and a power-on light both disposed on the housing, both the push-button and the power-on light being electrically connect to the circuit board.

4. The combination air filter and goggles of claim 1, further comprising a power socket disposed on the housing so that mains power is configured to supply to the power supply for charging by electrically connecting to the power socket.

5. The combination air filter and goggles of claim 1, further comprising an opening disposed through the circuit board and aligned with the inlet of the centrifugal fan.

6. The combination air filter and goggles of claim 1, further comprising a plurality of louvers disposed on the cover, and a battery cover disposed adjacent to the louvers and aligned with the power supply.

* * * * *